(12) United States Patent
Berzak et al.

(10) Patent No.: US 10,997,367 B2
(45) Date of Patent: May 4, 2021

(54) EYE TRACKING AS A LANGUAGE PROFICIENCY TEST

(71) Applicant: Massachusetts Institute of Technology, Cambridge, MA (US)

(72) Inventors: Yevgeni Berzak, Somerville, MA (US); Boris Katz, Cambridge, MA (US); Roger Levy, Somerville, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 405 days.

(21) Appl. No.: 16/130,627

(22) Filed: Sep. 13, 2018

(65) Prior Publication Data

US 2019/0080623 A1 Mar. 14, 2019

Related U.S. Application Data

(60) Provisional application No. 62/558,710, filed on Sep. 14, 2017, provisional application No. 62/558,765, filed on Sep. 14, 2017.

(51) Int. Cl.
*G06F 40/263* (2020.01)
*G06F 3/01* (2006.01)
(Continued)

(52) U.S. Cl.
CPC ........... *G06F 40/263* (2020.01); *G06F 3/013* (2013.01); *G06F 17/18* (2013.01); *G06F 40/30* (2020.01);
(Continued)

(58) Field of Classification Search
CPC ........ G06F 40/263; G06F 40/30; G06F 3/013; G06F 17/18; G06F 3/005; G06K 9/00604; G06K 9/0061; G06K 9/00617; G06K 9/00335; G09B 5/02; G09B 17/003; G09B 19/06; G06N 20/00; G06N 3/08; G16H 50/70; A61B 5/7267; A61B 5/163
(Continued)

(56) References Cited

U.S. PATENT DOCUMENTS

2019/0079917 A1 3/2019 Berzak

OTHER PUBLICATIONS

Rayner, K., "Eye Movements in Reading and Information Processing: 20 Years of Research", Psychological Bulletin, vol. 124, No. 3 (1998).

(Continued)

*Primary Examiner* — Thierry L Pham
(74) *Attorney, Agent, or Firm* — Hamilton, Brook, Smith & Reynolds, P.C.

(57) ABSTRACT

In an embodiment, Applicant's method can automatically determine proficiency in a given language by tracking a user's gaze during reading a sample text. The language proficiency test includes reading sentences in a language (e.g., a language to the user's native language). The user's, or learner's, gaze is recorded using an eye-tracking camera while they read the sample text. Applicant's method and corresponding system predicts the language proficiency of the learner based on their gaze patterns. Applicant's method and corresponding system can also predict performance on specific standardized language proficiency tests such as Michigan EPT (Michigan English Proficiency Test), TOEIC® (Test of English for International Communication®), and TOEFL® (Test of English as a Foreign Language®).

23 Claims, 6 Drawing Sheets

(51) Int. Cl.
  G06F 17/18   (2006.01)
  G06K 9/00    (2006.01)
  G06N 3/08    (2006.01)
  G06N 20/00   (2019.01)
  G06F 40/30   (2020.01)
  G09B 5/02    (2006.01)
  G09B 17/00   (2006.01)
  G09B 19/06   (2006.01)

(52) U.S. Cl.
  CPC ....... *G06K 9/0061* (2013.01); *G06K 9/00335* (2013.01); *G06K 9/00604* (2013.01); *G06K 9/00617* (2013.01); *G06N 3/08* (2013.01); *G06N 20/00* (2019.01); *G09B 5/02* (2013.01); *G09B 17/003* (2013.01); *G09B 19/06* (2013.01)

(58) Field of Classification Search
  USPC ......................................................... 434/169
  See application file for complete search history.

(56)  References Cited

OTHER PUBLICATIONS

Rayner, K., et al., "Psychology of Reading", 2nd Edition, Psychology Press (2012).
Berzak, Y., et al. "Predicting Native Language from Gaze", May 2, 2017.
Barrett, M., et al. "Reading behavior predicts syntactic categories", Proceedings of the 19th Conference Language Learning pp. 345-349, Beijing, China, Jul. 30-31, 2015.
Barrett, M., et al., "Using reading behavior to predict grammatical functions", Proceedings of the Sixth Workshop on Cognitive Aspects of Computational Language Learning, pp. 1-5, Lisbon, Portugal, Sep. 18, 2015.
Barrett, M., et al, "Weakly Supervised Part-of-Speech Tagging Using Eye-Tracking Data", Proceedings of the 54th Annual Meeting of the Association for Computational Linguistics, pp. 579-584, Berlin, Germany, Aug. 7-12, 2016.
Berzak, Y., et al, "Contrastive Analysis with Predictive Power: Typology Driven Estimation of Grammatical Error Distributions in ESL", 18th Conference on Computational Natural Language Learning, Mar. 24, 2016.
Berzak, Y., et al, "Reconstructing Native Language Typology from Foreign Language Usage", Center for Brains, Minds & Machines, May 28, 2014.
Brooke, J., et al., "Measuring Interlanguage: Native Language Identification with L1-influence Metrics", LREC, pp. 779-784, 2012.
Bykh, S., et al., "Advancing Linguistic Features and Insights by Label-informed Feature Grouping: An Exploration in the context of Native Language Identification", Proceedings of COLING 2016, the 26th International Conference on Computational Linguistics: Technical Papers, pp. 739-749, Osaka, Japan, Dec. 11-17, 2016.
Byrd, R.H., et al., "A Limited Memory Algorithm for Bound Constrained Optimization", Northwestern University, Dept of Electrical Engineering and Computer Science, May 1994.
Collins, C., et al., "Syntatic Structures of the World Languages", SSWL:directory:about, downloaded from internet http://sswl.railsplayground.net/about; Oct. 19, 2018.
Cop, U., et al., "Eye Movement Patterns in Natural Reading: A Comparison of Monolingual and Bilingual Reading of a Novel", PLOS One, 10(8):1-38, Aug. 19, 2015.
Dussias, P., et al. "Uses of Eye-Tracking Data in Second Language Sentence Processing Research", Annual Review of Applied Linguistics, 30, pp. 149-166, (2010).
Jarvis, S., et al., "Crosslinguistic Influence in Language and Cognition", Sociolinguistic Studies, vol. 6.3, pp. 603-607, 2012.
Klerke, S., et al. "Improving Sentence Compression by Learning to Predict Gaze", Proceedings of NAACL-HLT, pp. 1528-1533, 2016.
Koppel, M., et al., "Determining an Author's Native Language by Mining a Text for Errors", KDD '05, Aug. 21-24, 2005.
Lewis, M.P., et al., "Ethnologue: Languages of Ecuador", Ethnologue, 18th Edition, 2015.
Littel, P., et al. "URIEL and long2vec: Representing languages as typological, geographical, and phylogenetic vectors", Proceedings of the 15th Conference of the European Chapter of the Association for Computational Linguisitcs: vol. 2, pp. 8-14, Valencia, Spain, Apr. 3-7, 2017.
Malmasi, S., et al., "Language Transfer Hypotheses with Linear SVM Weights", EMNLP, pp. 1385-1390, 2014.
Marcus, M., et al. "Building a Large Annotated Corpus of English" The Penn Treebank, Oct. 1993. http://repository.upenn.edu/cis_reports.
McDonald, R., et al. "Universal Dependency Annotation for Multilingual Parsing", Proceedings of the 51st Annual Meeting of the Association for Computational Linguisitics, pp. 92-97, Sofia, Bulgaria, Aug. 4-9, 2013.
Nagata, R., "Language Family Relationship Preserved in Non-Native English", Proceedings of COLING, 2014, 25th International Conference on Computational Linguistics, pp. 1940-1949, Dublin, Ireland, Aug. 23-29, 2014.
Nagata, R., et al., "Reconstructing an Indo-European Family Tree from Non-native English Texts", Proceedings fo rhte 51st Annual Meeting of the Association of Computational Linguistics, pp. 1137-1147, Sofia, Bulgaria, Aug. 4-9, 2013.
Oldin, T., et al. "JALT Journal: Journal of the Japan Association of Language Teachers" Cambridge University, 11(2), Dec. 1989.
Petrov, S., "A Universal Part-of-Speech Tagset", LRCE, 2012.
Roberts, L., "Using Eye-Tracking to Investigate Topics in L2 Acquisition and L2 Processing", Studies in Second Language Acquisition (35(02):213-215, 2013.
Swanson, B., et al. "Data Drive Language Transfer Hypotheses", Proceedings of the 14th Conference of the European Chapter of the Association for Computational Linguistics, pp. 169-173, Gothenburg, Sweden, Apr. 26-30, 2014.
Swanson, B., et al., "Extracting the Native Language Signal", Proceedings of NAACL-HLT 2013, pp. 85-94, Atlanta, Georgia, Jun. 9-14, 2013.
Tetreault, J., et al. "A Report on the First Native Language Identification Shared Task", Proceedings of the Eighth Workshop on Innovative Use of NLP for Building Educational Applications, pp. 48-57, Atlanta, Georgia, Jun. 13, 2013.
Tsur, O., et al. "Using Classifier Features for Studying the Effect of Native Language on the Choice of Written Second Language Words", Proceedings of the Workshop on Cognitive Aspects of Computational Language Acquisition, pp. 9-16, Prague, Czech Republic, Jun. 2007.
Ward, J.H, "Hierarchical Grouping to Optimize an Objective Function", Journal of the American Statistical Association, vol. 58, No. 301 (Mar. 1963), pp. 236-244.
Yannakoudakis, H., et al. "A New Dataset and Method for Automatically Grading ESOL Texts", Proceedings of the 49th Annual Meeting of the Association for Computational Linguistics, pp. 180-189, Portland, Oregon, Jun. 19-24, 2011.
Martohardjono, G., et al. "Language transfer: what do we really mean", In L. Eubank, L. Selinker, and M. Sharwood Smith, editors, The current state of Interlanguage: studies in honor of William E. Rutherford, John Benjamins:The Netherlands, pp. 205-219, 1995.
Rosa, A., "Crosslinguistic Influence in Second Language Acquisition" vol. 95, Multilingual Matters. 2015.
Berkes, E, "Multilingual: New perspectives on syntactic development", The Handbook of Bilingualism and Multilingualism, Second Edition pp. 137-167, 2012.
Hammarstrom, H., "Max Planck Institute for Evolutionary Anthropology", Leipzig. Jan. 1, 2015 https://web.archive.org/web/20150101011442/https://glottolog.org/—downloaded from Internet Feb. 8, 2019.
Jarvis, S., et al. "Approaching Language Transfer Through Text Classification Explorations in the Detection-based Approach" vol. 64, Multilingual Matters. 2012.

(56) References Cited

OTHER PUBLICATIONS

Littel, P., et al. URIEL Typological Database. Pittsburgh:Carnegie Mellon University. http://www.cs.cmu.edu/ dmortens/uriel.html—downloaded from the Internet Feb. 7, 2019.
Piantadosi, S.T., et al., "Word Lengths are Optimized for Efficient Communication", Proceedings for the National Academy of Sciences, 108(9): 3526-3529. Dec. 2010.
Santorini, B., Part-of-Speech Tagging Guidelines for the Penn Treebank Project (3rd Revision), Technical Reports, (CIS) 1990.
Tetreault, J., et al. "Native Tongues, Lost and Found: Resources and Empirical Evaluations in Native Language Identification", Technical Papers, pp. 2585-2602, COLING, 2012.
Littel, P., et al. URIEL Typological Database. Pittsburgh:Carnegie Mellon University. http://www.cs.cmu.edu/ dmortens/uriel.html—downloaded from Internet Feb. 7, 2019.
Notice of Allowance for U.S. Appl. No. 16/130,662 dated Jan. 28, 2021 titled "Predicting Native Language From Gaze".
Corrected Notice of Allowance for U.S. Appl. No. 16/130,662 dated Feb. 5, 2021 titled "Predicting Native Language From Gaze".
PTO Response to Rule 312 Communication for U.S. Appl. No. 16/130,662 dated Mar. 19, 2021 titled "Predicting Native Language From Gaze".

|        | Word 1 | Word 2 | Word 3 | Word 4 | Word 5 | Word 6 | Word 7 | Word 8 | Word 9 |
|--------|--------|--------|--------|--------|--------|--------|--------|--------|--------|
| Word 1 |        |        |        |        |        |        |        |        |        |
| Word 2 |        | 1      |        |        |        |        |        |        |        |
| Word 3 |        |        | 2      |        |        |        |        |        |        |
| Word 4 |        |        |        | 3      |        |        |        |        |        |
| Word 5 |        |        | 1      |        | 2      |        |        |        |        |
| Word 6 |        |        |        |        |        | 1      |        |        |        |
| Word 7 |        |        |        |        |        |        | 2      |        |        |
| Word 8 |        |        |        |        |        | 2      |        | 3      |        |
| Word 9 |        |        |        |        |        |        |        |        | 4      |

Fig. 3  300

EYE TRACKING AS A LANGUAGE PROFICIENCY TEST

RELATED APPLICATIONS

This application claims the benefit of U.S. Provisional Application No. 62/558,710, filed on Sep. 14, 2017 and U.S. Provisional Application No. 62/558,765 filed on Sep. 14, 2017. This application is also related to U.S. application Ser. No. 16/130,662, filed on Sep. 13, 2018. The entire teachings of the above applications are incorporated herein by reference.

GOVERNMENT SUPPORT

This invention was made with Government support under Grant No. CCF-1231216 awarded by the National Science Foundation. The Government has certain rights in the invention.

BACKGROUND

Standardized language tests are used to determine proficiency in a given language. Such tests are subjectively judged on a test-taker's reading comprehension or writing abilities by a grader or against answers (e.g., of a multiple-choice test). Standardized tests have major drawbacks, however. Standardized tests can rely on manually created ad-hoc tasks, are prone to cheating, require test specific preparation and are expensive to develop.

SUMMARY

In an embodiment, Applicant's method can automatically determine proficiency in a given language by tracking a user's gaze during reading a sample text. The language proficiency test includes reading sentences in a given language (e.g., a language different from the user's native language). The user's, or learner's, gaze is recorded using an eye-tracking camera while they read the sample text. Applicant's method and corresponding system predicts the language proficiency of the learner based on their gaze patterns. Applicant's method and corresponding system can also predict performance on specific standardized language proficiency tests such as Michigan EPT (Michigan English Placement Test), TOEIC® (Test of English for International Communication®) and TOEFL® (Test of English as a Foreign Language®). While Applicant's method can predict performance for the Michigan EPT, TOEIC® and TOEFL®, Applicant's method can predict performance for the any language test, not just English proficiency tests.

Applicant's method and corresponding system measures language proficiency by the similarity of a user/learner's gaze patterns in reading to those of native speakers. In example embodiments, the method is language independent, and can therefore also be deployed for any language. Based on the outcome of the test, the system can also be extended to determine specific language skills that require improvement, and to recommend, to users (e.g., test takers), topics and materials to strengthen their language skills.

In an embodiment, the user reads a small set of sentences in a given language while eye-tracking is performed on the user. In one embodiment, each sentence is displayed to the user after a short gaze at a fixation point, and is presented as a one-liner. However, a person having ordinary skill in the art can recognize that a sample text can be presented at different levels of granularity (e.g., multiple sentences, paragraphs, pages, or fragments of a sentence). The user's eye-movement is recorded during sentence reading, resulting in data representing, for each time tracked, which word the user gazes at, which position or letter the user gazed at within each word, the time taken traveling between each word pair, and the path of words the user's gaze took during reading. The eye-tracking can track the user's gaze at each millisecond, e.g., at 1000 Hz. Each sentence is followed by a comprehension question to encourage attentive reading and to obtain a complementary measure of reading comprehension.

The technical approach for determining language proficiency includes two components. The first component is determining a set of gaze features that robustly characterize eye-movement patterns during reading. The set of gaze features enable reliably distinguishing between native and non-native readers, irrespective of their reading speed. The second component is comparing a learner's gaze patterns to those of native language speakers. This relation is currently implemented in two versions (a) measuring pattern similarity to a "prototype" native reader, and (b) probability of being native assigned by a native versus non-native classifier.

Applicant collected data from native and non-native users and readers, and developed a system for predicting language proficiency using the above described approach. Applicant's experiments suggest that this approach is highly effective in determining language proficiency:

First, the proficiency scores obtained with the eye tracking test correlate strongly with standardized tests, specifically with the Michigan English Placement Test (Michigan EPT) and TOEFL®. They also correlate well with user's answers to the reading comprehension questions. As such, the proposed approach can be used in combination with or as an alternative to traditional language tests. In other words, applicant's method can provide a proficiency score of a user representing the user's proficiency/linguistic capability with a given a language, and also provide a reading comprehension score of a passage, paragraph, etc.

Second, comparison of eye tracking test results to standardized tests can be used as a test diagnosis and calibration tool. For example, such a comparison reveals a well-known shortcoming of Michigan EPT, which is that the Michigan EPT is not well calibrated for advanced language learners.

Third, while Applicant's method is an alternative to standardized language testing, it can also be used to predict the outcome of specific standardized test scores with high accuracy using regression techniques. This prediction is done for the overall test score, and can also be extended to predict specific answers to questions in such tests.

Fourth, the eye tracking test scores are not only accurate, but also highly consistent. If the same user takes the test twice at around the same time, the user should receive similar scores in both tests.

In an embodiment, a method includes presenting, on a display, sample text in a given language to a user. The method further includes recording eye fixation times for each word of the sample text for the user and recording saccade times for each word pair that the user's gaze moves between fixations. The method further includes comparing features of the gaze pattern of the user to features of a gaze pattern of at least one training reader (e.g., training user) having a known proficiency of the given language. The method further includes generating a proficiency score of the user based on the results of the comparison.

In an embodiment, a method includes generating the features representing the gaze pattern of the user further by determining speed normalized features for words of the sample text.

In an embodiment, the method includes generating the features representing the gaze pattern of the user by determining speed normalized feature averages for clusters of words of the sample text. The clusters are based on part of speech labels, syntactic relation labels, information content, word identity, word length, word frequency, and word surprisal based on the recorded eye fixation times and saccade times. The features may include a first fixation duration (FF), first pass duration (FP), total fixation duration (TF), regression path duration (RP), word skips, saccade length, and landing location within the word.

In an embodiment, the method includes generating the features representing the gaze pattern of the user further by, for a sentence of the sample text, determining a scan path representing the sequence of fixations and saccades for the sample text. Determining the scan path for the sentence further includes generating a transition table having a number of rows and number of columns equal to the number of words in the sentence, where a first dimension of the table represents the word beginning a saccade and the second dimension of the table represents the word ending a saccade, and each entry in the table represents the number or fraction of saccades from the first word to the second word. A person having ordinary skill in the art can recognize, however, that other ways of representing the scan path and measuring scan path similarity are possible.

In an embodiment, fixations and saccades can be based on fixation and movement between words, word sequences, and other word groupings based on the syntactic or semantic structure of the sentence.

In an embodiment, the method can determine specific language skills that require improvement based on feature sets indicating deficiency in a language skill.

In an embodiment, the known proficiency is being a native speaker of the language.

In an embodiment, the results are a probability of being the native speaker or a similarity to a native speaker.

A person having ordinary skill in the art can recognize that the eye tracking record can be pre-processed in other ways than described herein, and transformed into other feature sets or other representations than the ones described herein. Such representations can divide the gaze trajectory into saccades and fixations, or use any other division of the eye tracking record into time periods, including using the location of the user's gaze at each individual sample time. The features can include any combination of the feature sets described herein, as well as any combination of other features, or a combination of both.

In an embodiment, a system measuring language proficiency can include a memory storing eye gaze patterns and gaze feature sets of a known proficiency of a given language, a processor coupled to the memory, a display monitor presenting sample text in the given language to a user, and a camera or eye tracker coupled to the processor. The camera is configured to record eye fixation times for each word of the sample text for the user and further configured to record saccade times for each word pair that the user's gaze moves between fixations. The processor is configured to receive the camera or eye tracker images and compare features of the gaze pattern of the user to features of a gaze pattern of at least one training reader (e.g., training user) having a known proficiency of the given language. The processor is further configured to generate a proficiency score of the user based on the results of the comparison.

A non-transitory computer-readable medium is configured to store instructions for determining language proficiency of a user. The instructions, when loaded and executed by a processor, causes the processor to present, on a display, sample text in a given language to a user. The instructions further cause the processor to record eye fixation times for each word of the sample text for the user. The instructions further cause the processor to record saccade times for each word pair that the user's gaze moves between fixations. The instructions further cause the processor to compare features of the gaze pattern of the user to features of a gaze pattern of at least one training reader (e.g., training user) having a known proficiency of the given language. The instructions further cause the processor to generate a proficiency score of the user based on the results of the comparison.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 3 illustrates an example embodiment of a scan path table having nine words.

DETAILED DESCRIPTION

A description of example embodiments follows.

Figure 1:
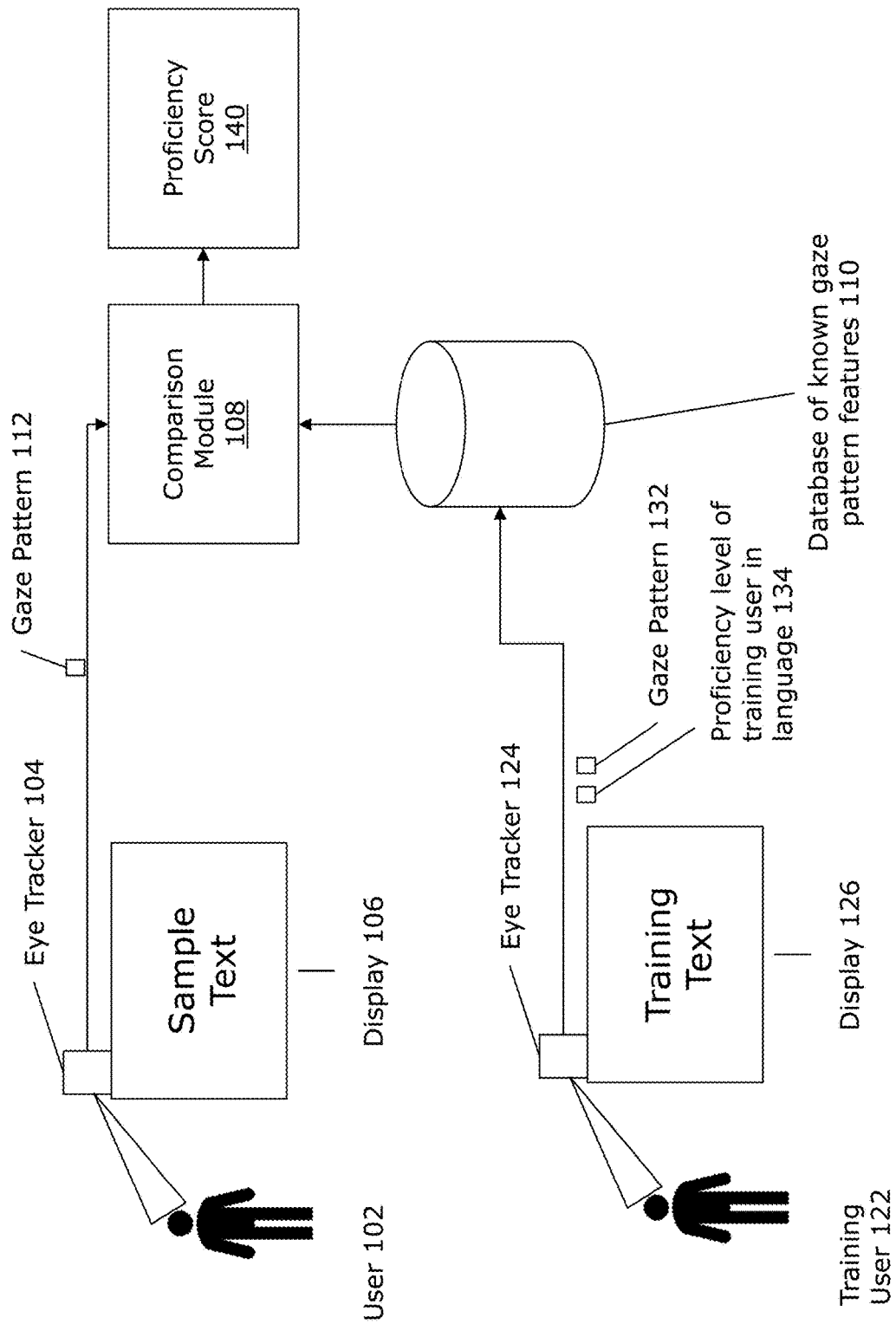
FIG. 1 is a block diagram illustrating an example embodiment of the present technology.

FIG. 1 is a block diagram 100 illustrating an example embodiment of the present technology. First, training user(s) 122 read a training text on a display 126 while an eye tracker 124 captures images of the training user's 122 eyes. The eye tracker 124 captures the movement of the user's gaze (e.g., of the user's eyes) relative to the display 126, and can capture the location or position of a user's gaze for each period of time. In one embodiment, the eye tracker 124 captures the focus of the user's eye at each millisecond (e.g., 1,000 Hz). The data the eye tracker 124 outputs is referred to in FIG. 1 as a gaze pattern 132. The gaze pattern 132 can include the raw images of the user's eye, or data relating to fixations and saccades of the user's text. The fixation and saccade data can indicate which words or spaces the user's eye is focused on in a given frame, or be even more granular and indicate which character or letter the user's eye is focused on.

The system uses gaze pattern 132 from users 122 to obtain a model which can be a regression model (e.g., Ridge regression) or classifier (e.g., logistic regression, nearest neighbors, or neural network), or an average gaze pattern representation. Each gaze pattern 132 is associated with a level of proficiency of the training user (e.g., a normalized TOEFL® or other test score). The system trains the model (e.g., database 110) based on the gaze pattern 132 and the proficiency level 134 of the training user 122 in the language. In an embodiment, the classifier is a logistic regression classifier, but a person having ordinary skill in the art can recognize that other classifiers and neural network classifiers can be employed.

After the model is trained, the system can test a user's 102 proficiency. A display 106 displays a sample text to the user. While the user 102 reads the sample text, an eye tracker 104 tracks the user's eyes. In one embodiment, the sample text can be a same text as the training text, but in another embodiment can be a different text. Both embodiments are described below in further detail. Like eye tracker 124, the eye tracker 104 captures movements of the user's 102 eyes relative to the display 106, and can capture the focus of a user's eye for each period of time. The features of the eye tracker 104 and 124 can interchangeable, and in embodiments can be the same eye tracker.

The eye tracker 104 outputs a gaze pattern 112 of the user 102. A comparison module 108 compares the gaze pattern of the user 102 reading the sample text using the model trained on the features extracted from the training users 122 reading training texts. Based on the comparison, the system outputs a proficiency score 140. This proficiency score can replace standardized language proficiency tests.

Figure 2:
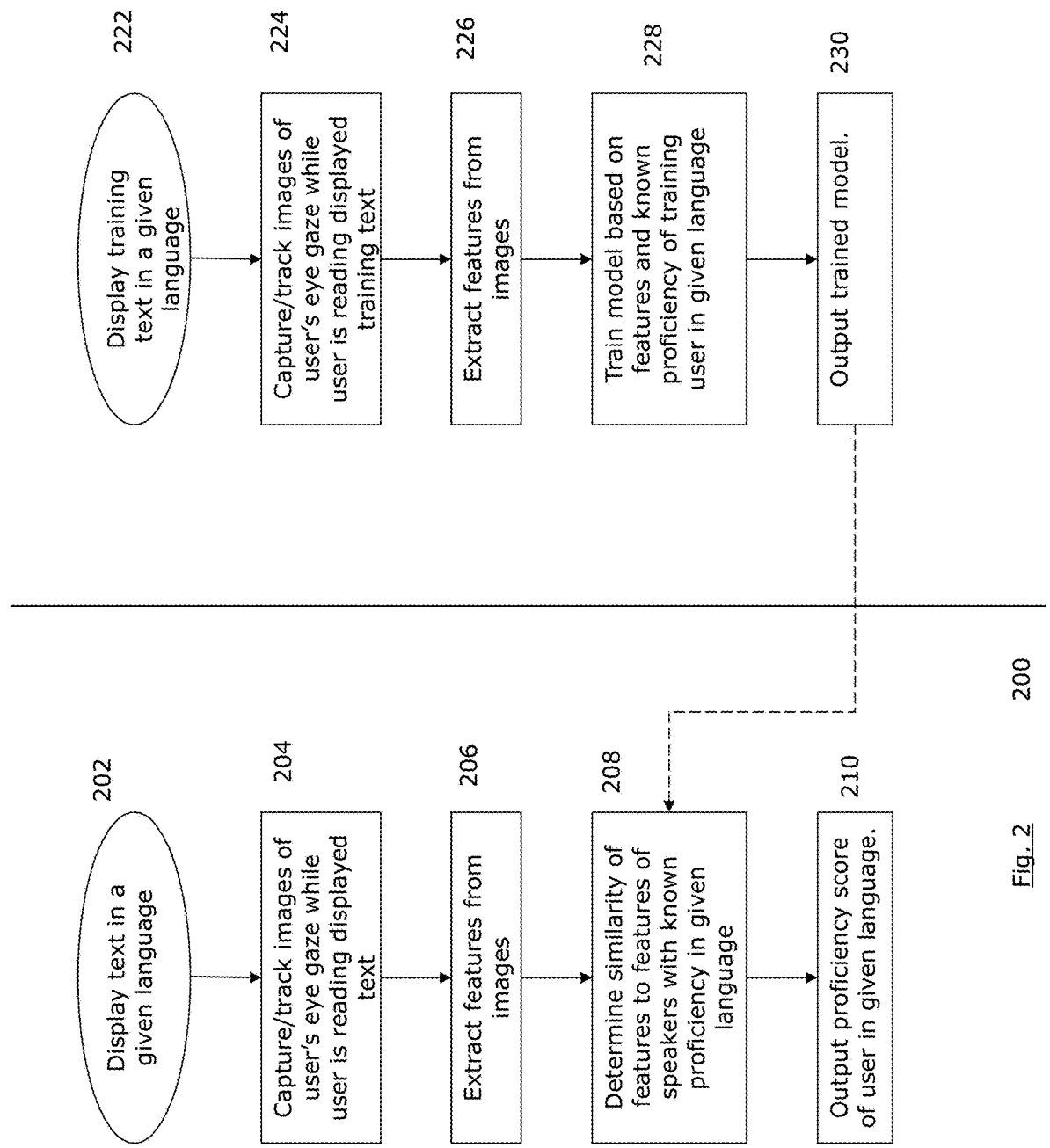
FIG. 2 is a flow diagram illustrating an example embodiment of the present technology.

FIG. 2 is a flow diagram 200 illustrating an example embodiment of the present technology. FIG. 2 illustrates two methods in parallel: a testing method (202-210) and a training method (222-230), however, these methods are linked and can be performed in parallel. For example, training can continue to add data the trained model while testing is underway. However, to aide in the description of both methods, training is described first below.

In training, text is displayed to a user in a given language (222). The method captures/tracks images of a user's eye gaze while the user is reading displayed training text (224). The method extracts features from the images (226). These features can be low-level features, based on or derived from saccades and fixations, or higher level linguistic features, as described in further detail below. From the features, the method trains the model based on features and a known proficiency of the training user in a given language (228), and outputs that trained model (230).

In testing a user, the method displays text in a given language to a user (202). The method then captures/tracks images of the user's gaze while user is reading displayed text (204). The method extracts features from the images (206). These features can be low-level features, based on or derived from saccades and fixations, or higher level linguistic features, as described in further detail below. The method compares the extracted features from the testing user using the outputted trained model 230 (208). Then, based on the comparison, the method outputs a proficiency score of the testing user in the given language (210).

Applicant's eye tracking language proficiency test has users read a small set of sentences written in a given language. Each portion of the sample text appears on a blank screen as a one liner. An example portion size is a single sentence, however, a person having ordinary skill in the art can recognize that the portion can be multiple sentences, paragraphs, multiple paragraphs, or portions of sentences. Upon the user completing reading the portion, the user is asked to answer a comprehension question (e.g., Boolean question, multiple choice question, or other type of comprehension question) about the sentence. The questions are introduced to encourage attentive reading and to obtain a complementary measure of reading comprehension. Both the sentences and the questions are triggered by a short gaze of 300 ms on a fixation target which appears on a blank screen and is co-located with the beginning of the text in the following screen. Users and training readers can use a controller to indicate reading completion and to answer the comprehension questions. Note that this setup can be modified in various ways, including presentation of multiple sentences at a time or omission of fixation targets and reading comprehension questions.

The reading material of the test consists of random or arbitrary subject language sentences, for example random or arbitrary language sentences. There is no restriction on the form and content of the sentences, and they can be obtained from any textual source, or in another embodiment, written for the system. In an embodiment, randomly selected newswire sentences can be used. A database includes annotations of sentences having linguistic information, including part-of-speech tags and syntactic trees, however, these annotations are not displayed to the user.

Applicant's method generates produces two types of scores: (1) an: "eye-tracking Score" that is a standalone language proficiency score based on the reader's gaze patterns, and (2) "External Test Scores" that predictions for expected performance on external standardized English tests such as TOEFL® and Michigan EPT. All the scores are produced automatically after test completion and subsequent analysis.

Applicant's method can further implement two variants of the test. A first variant can be referred to as a "Fixed Text" test. In the Fixed Text version, the test is developed and deployed using a fixed set of pre-selected sentences. In preparation for deploying the test, gaze data from multiple readers is collected for a single set of sentences. This gaze data is used to build a model of features of an expected gaze pattern of a native speaker of the language, or a speaker with a given proficiency. The language proficiency of a user (e.g. test taker) then is evaluated by comparing the features of the user's (e.g., test taker's) gaze patterns on that same set of sentences to the features of the model.

A second variant can be referred to as the "Any Text" version. In this version of the test, both development and deployment can be performed with different sentences presented to each reader. In other words, the test can employ more than just a pre-chosen set of sentences. The proficiency of a user (e.g., test taker) can accordingly be evaluated based on their reading patterns of any set of sentences. This capability dramatically increases the applicability of the test and reduces the cost of test development.

Eye movement during reading is known to be closely related to linguistic characteristics of the text and reflects ways in which readers engage with the text (Rayner 1998, Rayner, et al. 2012). Applicant's method leverages these principles to introduce a novel, cognitively driven technology for analyzing eye-tracking records and using them to determine language proficiency.

Applicant's approach includes two key components. The first component is a collection of gaze feature sets which robustly summarize eye movement during reading. The feature sets provide linguistically motivated characterizations of gaze trajectories which enable highly informative comparisons of reading patterns across different readers, and crucially, across different sentences. The second component comprises mechanisms for prediction of language proficiency via matching of learner gaze features and native gaze features, and correlation of gaze in reading with external proficiency scores.

In Applicant's method, eye-tracking devices record the location of the reader's gaze over time. An example sampling rate of an eye tracker is 1,000 Hz. Eye trackers may have other specifications or parameters that can impact the quality of the collected data as well. Applicant transforms this recording into several feature sets which summarize the reading patterns of the reader. Applicant's features are linguistically motivated and designed to be robust to uninformative variation stemming from personal reading styles.

The features are based on an established division of the gaze trajectory to fixations (stops) and saccades (movements between fixations). In particular, several feature sets use one or more or a combination of any of the following reading metrics, however, other reading metrics can be used:
  a) First Fixation Duration (FF)—duration of the first fixation on a word.
  b) First Pass Duration (FP)—time spent from gaze first entering a word to gaze first leaving it, which includes re-fixations within the word.
  c) Total Fixation Duration (TF)—the sum of all fixation times on a word.
  d) Regression Path Duration (RP)—the time from first entering a word until proceeding to its right.
  e) Word Skips—whether the word was skipped or read.
  f) Saccade Length—the distance between two fixations.
  g) Landing location within a word—the location (e.g., a 0-1 normalized position or character) of the first fixation on a word.
  h) Saccade direction—the direction (e.g., forward or backwards) of the saccade.
  i) Number of fixations—the total number of fixations.
  j) Number of regressions—the number of saccades with a backwards saccade direction.

Another feature set are word property coefficients, which measure the extent to which linguistic properties of words, such as word length, word frequency, and word surprisal, influence reading times (FF, FP, TF, RP, and word skips).

Bigram, and trigram sequences are referred to as $seq_{i,k} = w_i, \ldots, w_{i+k-1}, k \in \{1, 2, 3\}$, where for each metric $M \in (FF, FP, TF, RP)$ the fixation time for a sequence $M_{seq_{i,k}}$ is defined as the sum of fixations on individual tokens $M_w$ in the sequence.

$$M_{seq_{i,k}} = \Sigma_{w' \in seq_{i,k}} M_{w'} \quad (1)$$

A person having ordinary skill in the art can recognize that the sequences can be expanded to higher order ngrams or non-consecutive word groups in the sentence (e.g., based on syntactic or semantic relations between words). Further, operations other than summation of reading times can be used.

Another aspect of the eye-tracking language test is that it controls for the reading speed of the reader. Applicant's method can perform better in certain embodiments without speed normalization, such as regression on external proficiency scores, but in many embodiments, speed normalization improves performance. The above listed fixation duration measures are normalized for each word as follows to minimize the variable of reading speed of the reader. First, Applicant's method defines a normalization constant as a metric's fixation time per word in the word's context. For feature sets applicable only to the Fixed Text embodiment, the context is defined as the sentence in which the word appears. For features applicable to both the Fixed Text and Any Text embodiments, the context is the entire textual input presented to the reader. Applicant's method then obtains a normalized fixation duration metric by dividing the word's fixation metric by this term. However, other methods of speed normalization are possible.

Therefore, for each metric M and sequence $seq_{i,k}$, the method normalizes the sequence fixation time $M_{seq_{i,k}}$ relative to the subject's sequence fixations times in the textual context of the sequence. The context C is defined as the sentence in which the sequence appears for the Words in Fixed Context feature-set and the entire textual input for the cluster based feature-sets, as described below. The normalization term $S_{M,C,k}$ is defined as the metric's fixation time per sequence of length k in the context:

$$S_{M,C,k} = \frac{1}{|C|} \sum_{seq_k \in C} M_{seq_k} \quad (2)$$

The method can then obtain a normalized fixation time $M_{norm\,seq_{i,k}}$ as:

$$M_{norm\,seq_{i,k}} = \frac{M_{seq_{i,k}}}{S_{M,C,k}} \quad (3)$$

The Fixed Text embodiment includes the following feature sets.

Words in Fixed Context: This feature set includes a speed normalized FF, FP and TF for individual words appearing in a fixed context across readers. This is a token-based feature set, which requires the same textual input for all users and training readers, and is thus applicable only in the Fixed Text regime.

Scan Path: This feature set includes an N×N transition table M between words, for a sample having N words. Each entry of the Table M, M(i,j), indicates the number of saccades from word i to word j. These counts are normalized by the total number of saccades recorded during sentences reading. Similar to Words in Fixed Context, this feature set is applicable only when gaze data from multiple subjects is available for the same given sentence that the testing user reads.

FIG. 3 illustrates an example embodiment of a scan path table having nine words (e.g., N=9). Each number can represent a number of saccades from one word to the next. For example, from Word 1 to Word 2, there is 1 saccade unit indicated by the table of FIG. 3. A person having ordinary skill in the art can recognize that saccades are listed from each word to the next word. However, saccades can also be recorded for words read out of order. For example, the table indicates a saccade is recorded for the reader moving its gaze from word 4 backwards to word 3 for 1 saccade units, and word 7 backwards to word 6 for two saccade units The Any Text embodiment includes the following feature sets. However, the fixed set embodiment can also include these feature sets.

Reading Time Coefficients: The reading time coefficients of regression models that predict word reading times (FF, FP, TF, Word Skipping and RP) from word characteristics such as length, frequency, and surprisal (currently implemented as trigram probability).

Saccade Length: Average saccade length

Landing Site: average first fixation position within a word (normalized, e.g., on a scale of 0 to 1).

Linguistic Clusters: Average speed normalized FF, FP and TF for words clustered by part-of-speech tags, syntactic relation labels and information content (e.g., a metric that can be approximated using word length), word length, information content, word frequency, word surprisal, and word identity. As described below, this abstraction over gaze trajectories is effective both in the Any Text and the Fixed Text embodiments. The respective feature set can be extended to include additional linguistic clustering criteria.

Each feature set is pre-processed for each individual feature by deriving a zero mean unit variance scaler from the training set feature values, and applying the scaler to transform both the training and test values of the feature to Z scores.

In one embodiment, the method employs individual words as units of analysis. In another embodiment, the method computes fixation based features for word sequences (ngrams or n-grams) and other word groupings (e.g. based on the syntactic structure of the sentence).

Figure 4:
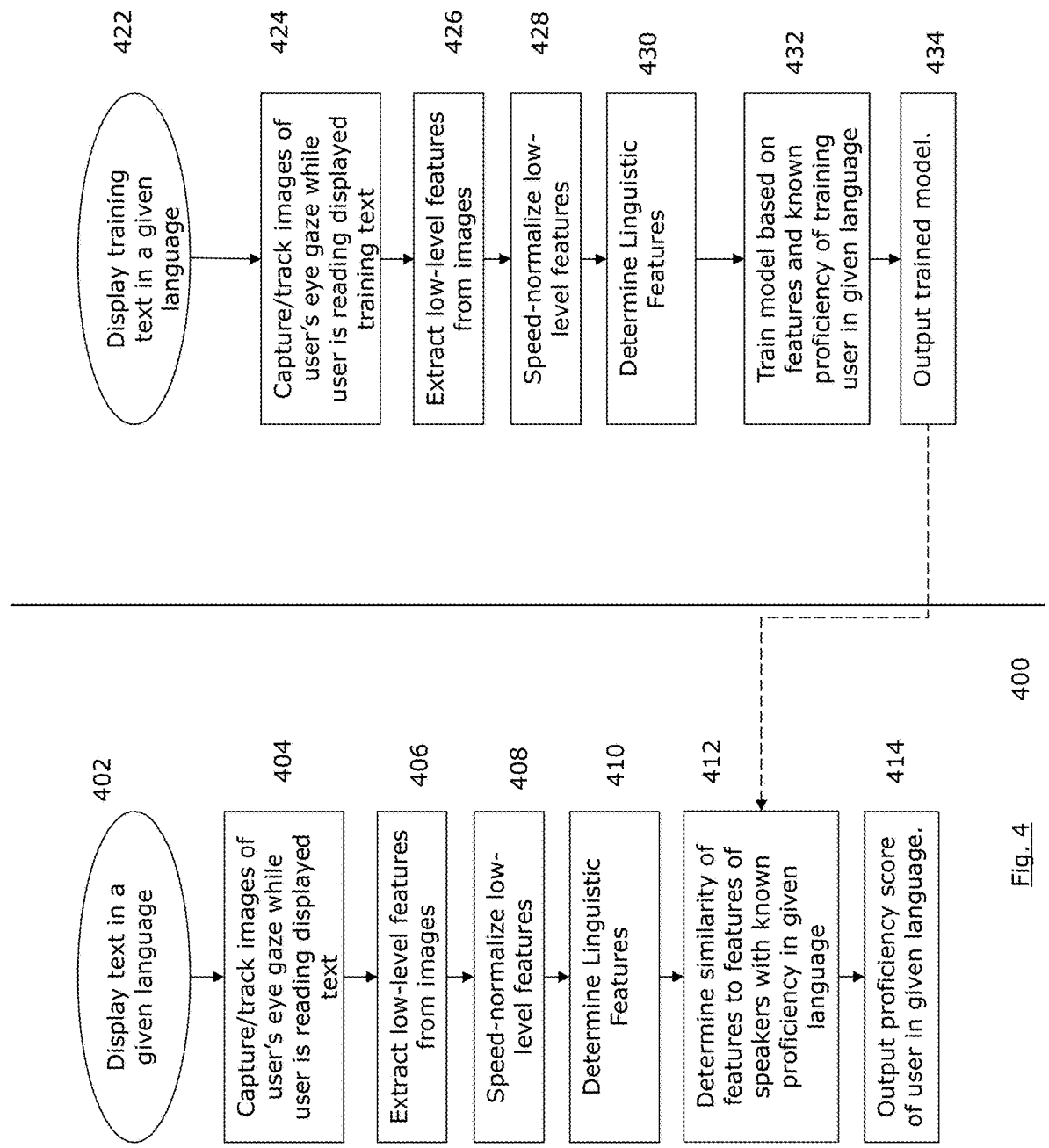
FIG. 4 is a flow diagram 400 illustrating a method employed by an embodiment of the present invention.

FIG. 4 is a flow diagram 400 illustrating a method employed by an embodiment of the present invention. FIG. 4 illustrates two methods in parallel: a testing method (402-414) and a training method (422-434), however, these methods are linked and can be performed in parallel. For example, training can continue to add data the trained model while testing is underway. However, to aide in the description of both methods, training is described first below.

In training, text is displayed to a user in a given language (422). The method captures/tracks images of a user's eye gaze while the user is reading displayed training text (424). The method extracts low-level features from the images, where low-level features are based on fixations and saccades (426). The method then speed-normalizes the low-level features (428), as described in relation to Equations 1-3 above. From the speed normalized features, the method calculates higher level linguistic cluster features (430). From the features, the method trains the model based on features and a known proficiency of the training user in a given language (432), and outputs that trained model (434).

In testing a user, the method displays text in a given language to a user (402). The method then captures/tracks images of the user's gaze while user is reading displayed text (404). The method extracts low-level features from the images (406). The method then speed-normalizes the low-level features (428), as described in relation to Equations 1-3 above. From the speed normalized features, the method calculates higher level linguistic cluster features (430). From these higher level features, the method determines a similarity of features with speakers having a known proficiency in the given language (412). For example, one comparison may be of fixation times for a given part of speech (e.g., nouns, verbs, determiners, prepositions, etc.). Then, based on the comparison, the method outputs a proficiency score of the testing user in the given language (414).

Applicant's novel method employs the above described features to evaluate the language proficiency of the reader. Applicant's method employs predictive models that generate the eye-tracking score and the external test scores (e.g., TOEFL® Michigan EPT) as described below.

Applicant's method outputs an independent language proficiency score that measures the extent to which the user's (e.g., test taker's) gaze patterns during reading a sample text resemble those of native speakers. To produce this score, Applicant's method computes an average "prototype" feature representation of reading patterns obtained from native speakers. The language proficiency score of a non-native user (e.g., test taker) is then derived by comparing their gaze features to this prototype using a similarity metric. In another embodiment, a model outputs a probability of being a native speaker as the language proficiency score.

In other words, Applicant's method can extract information from native speakers or speakers with a known proficiency, such as information on saccade and fixation length for various syntactic information like parts of speech, or high and low information content words, and compare those metrics to those of a reader being tested. Based on those metrics, the method can develop a proficiency score of the reader.

In addition to the model that produces the eye-tracking score, an embodiment further predicts the reader's performance on external standardized language tests. This prediction is performed by fitting a regularized regression model with eye-tracking features as input and a score on an external language test as output. This embodiment calibrates the model with respect to native readers by including their gaze patterns mapped to perfect test scores to the training set of the regression model. The model currently predicts scores for TOEFL®, TOEIC® and Michigan EPT. Applicant's method further can predict the number of correctly answered comprehension questions on the eye-tracking test.

Applicant's method further includes an end-to-end system implementing the above described approach. Applicant has further tested its method and system using data collected from 37 native and 145 non-native users and training readers. Applicant's experiments suggest that embodiments are highly effective in determining language proficiency.

The proposed eye-tracking scores correlate strongly with scores on TOEFL®, TOEIC® and Michigan EPT, and correlates with scores on the reading comprehension questions.

The test scores of Applicant's method described herein predict the outcome of external standardized tests with high accuracy. While these predictions are currently provided for overall test scores, Applicant's system and method can also be extended to predict answers to specific questions in such tests. Comparison of eye-tracking scores to scores on external tests can be used to diagnose and calibrate such tests.

Applicant performed a split-half analysis, comparing scores on separate groups of sentences for the same reader. The split-half analysis suggests that eye-tracking based test scores are not only accurate, but also likely to be consistent across several tests taken by the same user.

In the analysis, the highest performance in the Fixed Text regime is currently obtained using the Words in Fixed Context feature set, while the best performing feature set applicable to both the Fixed Text and Any Text regimes is Syntactic & Information Clusters. However, other feature sets may perform highly when tested on different readers or different sample text.

Applicant's system remains highly accurate and robust in the Any Text regime, with only minor performance decreases in comparison to the Fixed Text regime. Obtaining reliable proficiency scores on any set of sentences without training data (e.g., gaze data from prior readers for the same sentences) increases the uses and commercial applications of Applicant's method.

No previous system predicts language proficiency from gaze. Embodiments of Applicant's method have several important advantages compared to existing language tests (e.g. Michigan EPT, TOEFL®, TOEIC®, IELTS, EF SET and others).

Applicant's method is more reliable because an eye-tracking test directly measures cognitive linguistic ability rather than relying on ad-hoc and handcrafted test questions.

Applicant's method is a robust solution to cheating because users do not know what exactly is being measured and cannot manipulate their eye movement to obtain higher scores, tests by embodiments are likely to be robust to cheating and test specific training.

Applicant's method is cheaper to develop because traditional language testing requires composing and piloting new test editions on a regular basis. This is costly, as well as time/labor intensive. Applicant's approach removes most of the need for labor because the test material is simply text.

Applicant's method is cheaper to administer. Standardized test fees are high because they are expensive to develop. For example, taking the TOEFL® test currently costs around $200, a price that is unaffordable for many potential users (e.g., test takers). Cheaper test development using eye-tracking implies more affordable costs for users (e.g., test takers), and the cost may decrease further because eye-tracking technology is constantly getting cheaper and more precise. Test preparation costs (e.g., purchasing practice tests) should also be reduced, as Applicant's technology does not require test specific practice.

Applicant's method is more convenient to take because sufficient eye-tracking precision may be able to be obtained using cheap wearable eye trackers, as well as regular cameras on laptops and mobile devices. These advancements can enable using embodiments from any location at any time.

Applicant's method is also likely to be more consistent relative to standardized tests.

There are currently over 1.5 billion English learners around the world, which creates enormous economic potential for a cheaper, more reliable and more convenient language proficiency test. The trend towards cheaper and more precise wearable eye trackers, discussed above, and development of tracking capabilities using cameras on laptops and mobile devices are likely to increase the commercial potential of Applicant's method over time.

There are at least two commercial applications for Applicants' technology:

1) The main application is a standalone language test, as an alternative (or addition) to existing standardized language tests. The technology (embodiments) enables producing both an independent proficiency score, and a prediction for the user's (test taker's) results on various standardized language tests.

2) A second application is a tool for diagnosing and calibrating standardized language tests (Michigan EPT, TOEFL®, etc . . . ).

In addition to end users, Applicant's method can be valuable to language testing companies like ETS, Education First, and Cambridge Assessment. Such companies can integrate Applicant's method with their products in various ways, including tracking gaze while performing existing standardized language tests, as an add-on to those tests, and as the previously mentioned test calibration tool.

The technology is also applicable to other languages, many of them (e.g. Chinese, German, French, and others) have a large number of learners around the world. Extensions of the system/invention technology can recommend users (e.g., test takers) learning materials based on their gaze patterns. Such capabilities can allow to use Applicants' technology not only as a language evaluation tool but also as a language learning tool.

Finally, variants of Applicant's embodiments and system can be used in the future for assessment of reading comprehension in native speakers.

Figure 5:
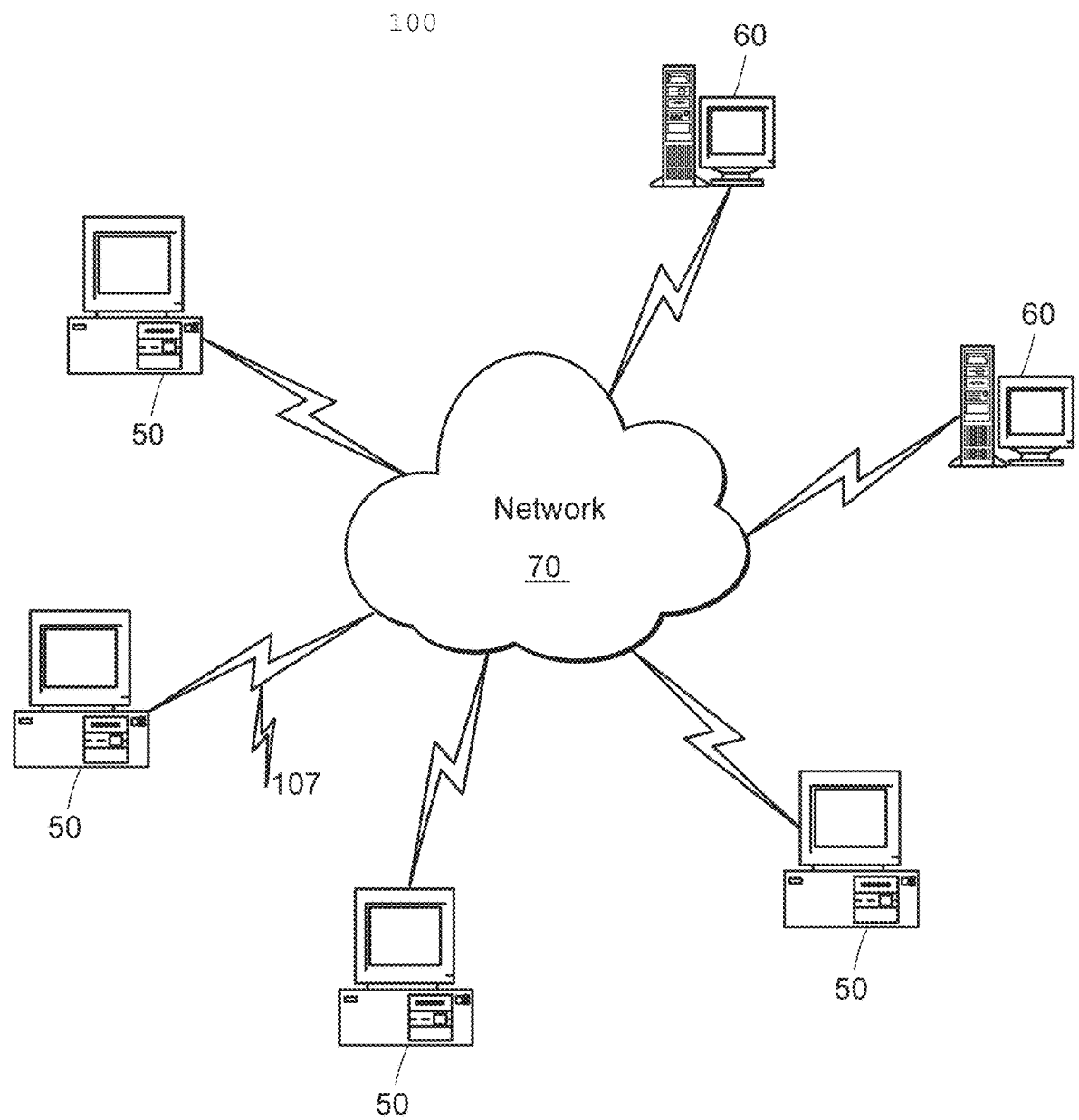
FIG. 5 illustrates a computer network or similar digital processing environment in which the present invention may be implemented.

FIG. 5 illustrates a computer network or similar digital processing environment in which the present invention may be implemented. Embodiments include systems 100, devices 50, 60, (FIG. 1) methods (FIG. 2, 4), computer program products (FIG. 5, 6), and other implementations, and are generally referenced 100 in the Figures.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), cloud computing servers or service, a worldwide collection of computers, Local area or Wide area networks, and gateways that currently use respective protocols (TCP/IP, Bluetooth, etc.) to communicate with one another. Other electronic device/computer network architectures are suitable.

Figure 6:
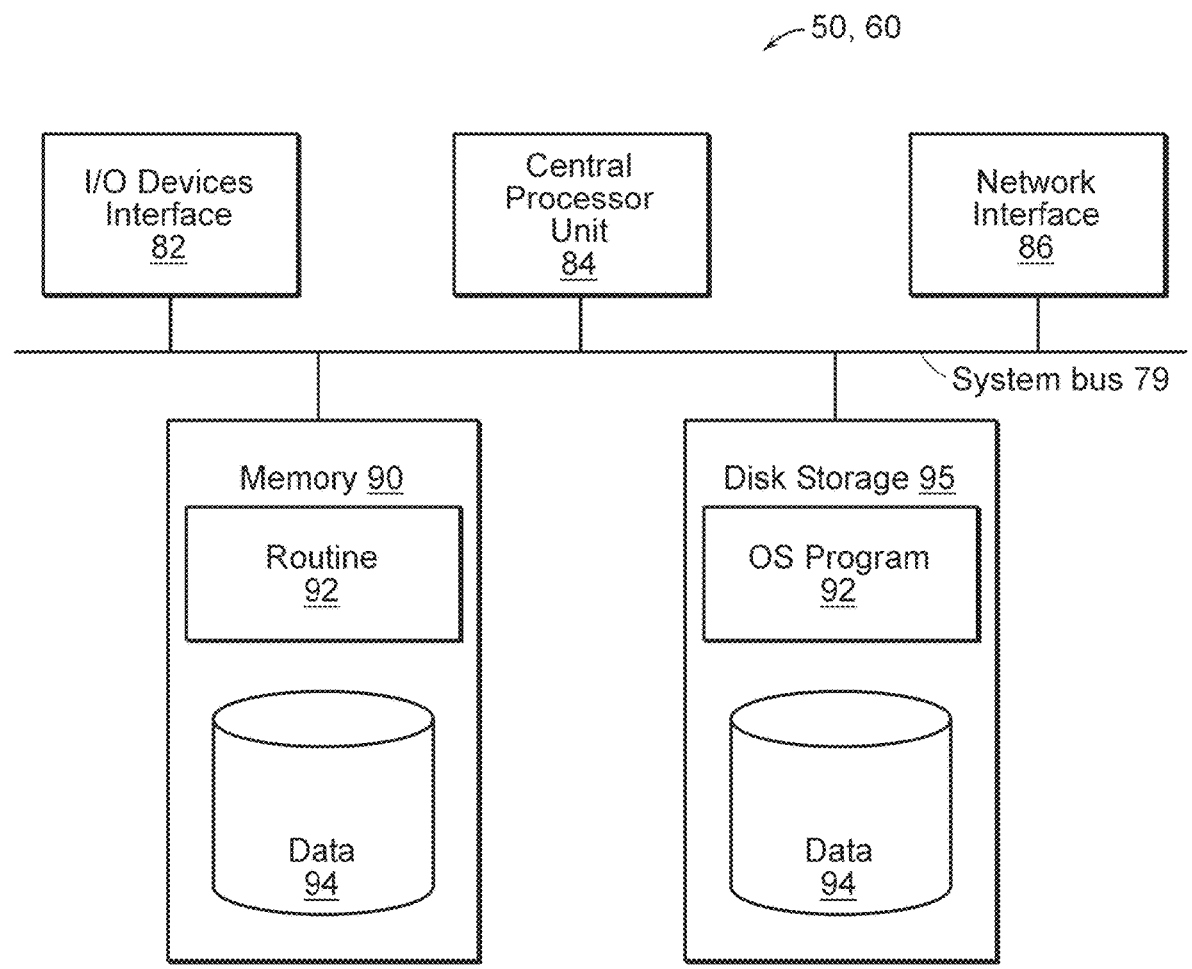
FIG. 6 is a diagram of the internal structure of a computer (e.g., client processor/device or server computers) in the computer system of FIG. 5.

FIG. 6 is a diagram of the internal structure of a computer (e.g., client processor/device 50 or server computers 60) in the computer system of FIG. 5. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 1). Memory 90 provides volatile storage for computer software instructions 92 and data 94 used to implement an embodiment of the present invention (e.g., code detailed above and in FIG. 3). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

In other embodiments, the program product 92 may be implemented as a so called Software as a Service (SaaS), or other installation or communication supporting end-users.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method comprising:
presenting, on a display, sample text in a given language to a user;
recording eye fixation times for each word of the sample text for the user;
recording saccade times for each word pair that the user's gaze moves between fixations;
comparing features of the gaze pattern of the user to features of a gaze pattern of at least one training reader having a known proficiency of the given language; and
generating a proficiency score of the user based on the results of the comparison.

2. The method of claim 1, further comprising:
generating the features representing the gaze pattern of the user further by determining speed normalized features for words of the sample text.

3. The method of claim 1, further comprising:
generating the features representing the gaze pattern of the user by determining speed normalized feature averages for clusters of words of the sample text, the clusters based on part of speech labels, syntactic relation labels, information content, word identity, word length, word frequency, and word surprisal based on the recorded eye fixation times and saccade times.

4. The method of claim 3, wherein the features include one or more of first fixation duration (FF), first pass duration (FP), total fixation duration (TF), regression path duration (RP), word skips, saccade length, and landing location within the word.

5. The method of claim 1, wherein the features include word property coefficients.

6. The method of claim 1, further comprising:
generating the features representing the gaze pattern of the user further by, for a sentence of the sample text, determining a scan path representing a sequence of fixations and saccades for the sample text.

7. The method of claim 6, wherein determining the scan path for the sentence further includes generating a transition table having a number of rows and number of columns equal to the number of words in the sentence, where a first dimension of the table represents the word beginning a saccade and the second dimension of the table represents the word ending a saccade, and each entry in the table represents the number or fraction of saccades from the first word to the second word.

8. The method of claim 1, wherein fixations and saccades can be based on fixation and movement between: words, word sequences, and other word groupings based on the syntactic or semantic structure of the sentence.

9. The method of claim 1, further comprising determining specific language skills that require improvement based on feature sets indicating deficiency in a language skill.

10. The method of claim 1, where the known proficiency is being a native speaker of the language.

11. The method of claim 1, wherein the results are a probability of being a native speaker.

12. A system measuring language proficiency comprising:
a memory storing eye gaze patterns and gaze feature sets of a known proficiency of a given language;
a processor coupled to the memory;
a display monitor presenting sample text in the given language to a user; and
a camera or eye tracker coupled to the processor and configured to record eye fixation times for each word of the sample text for the user and further recording saccade times for each word pair that the user's gaze moves between fixations;
the processor receiving the camera or eye tracker images and comparing features of the gaze pattern of the user to features of a gaze pattern of at least one training reader having a known proficiency of the given language, and generating a proficiency score of the user based on the results of the comparison.

13. The system of claim 12, wherein the processor is further configured to:
generate the features representing the gaze pattern of the user further by determining speed normalized features for words of the sample text.

14. The system of claim 12, wherein the processor is further configured to:
generate the features representing the gaze pattern of the user by determining speed normalized feature averages for clusters of words of the sample text, the clusters based on part of speech labels, syntactic relation labels, information content, word identity, word length, word frequency, and word surprisal based on the recorded eye fixation times and saccade times.

15. The system of claim 14, wherein the features include one or more of first fixation duration (FF), first pass duration (FP), total fixation duration (TF), regression path duration (RP), word skips, saccade length, and landing location within the word.

16. The system of claim 12, wherein the features include word property coefficients.

17. The system of claim 12, wherein the processor is further configured to:
generate the features representing the gaze pattern of the user further by, for a sentence of the sample text, determining a scan path representing the sequence of fixations and saccades for the sample text.

18. The system of claim 17, wherein determining the scan path for the sentence further includes generating a transition table having a number of rows and number of columns equal to the number of words in the sentence, where a first dimension of the table represents the word beginning a saccade and the second dimension of the table represents the word ending a saccade, and each entry in the table represents the number or fraction of saccades from the first word to the second word.

19. The system of claim 12, wherein fixations and saccades can be based on fixation and movement between: words, word sequences, and other word groupings based on the syntactic or semantic structure of the sentence.

20. The system of claim 12, wherein the processor is further configured to determine specific language skills that require improvement based on feature sets indicating deficiency in a language skill.

21. The system of claim 12, where the known proficiency is being a native speaker of the language.

22. The method of claim 12, wherein the results are a probability of being a native speaker.

23. A non-transitory computer-readable medium configured to store instructions for determining language proficiency of a user, the instructions, when loaded and executed by a processor, causes the processor to:
    present, on a display, sample text in a given language to a user;
    record eye fixation times for each word of the sample text for the user;
    record saccade times for each word pair that the user's gaze moves between fixations;
    compare features of the gaze pattern of the user to features of a gaze pattern of at least one training reader having a known proficiency of the given language; and
    generate a proficiency score of the user based on the results of the comparison.

* * * * *